United States Patent
Grosser et al.

(10) Patent No.: US 8,188,129 B2
(45) Date of Patent: May 29, 2012

(54) (−)-ENANTIOMER OF THE 2-[2-(1-CHLORO-CYCLOPROPYL)-3-(2-CHLOROPHENYL)-2-HYDROXYPROPYL]-2,4-DIHYDRO-[1,2,4]-TRIAZOLE-3-THIONE

(75) Inventors: Rolf Grosser, Leverkusen (DE); Manfred Jautelat, Leverkusen (DE); Astrid Mauler-Machnik, Leverkusen (DE); Stefan Dutzmann, Leverkusen (DE); Gerd Hanβler, Leverkusen (DE); Klaus Stenzel, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 32 days.

(21) Appl. No.: 11/981,050

(22) Filed: Oct. 31, 2007

(65) Prior Publication Data

US 2008/0113864 A1     May 15, 2008

Related U.S. Application Data

(63) Continuation of application No. 09/958,551, filed as application No. PCT/EP00/03066 on Apr. 6, 2000, now abandoned.

(30) Foreign Application Priority Data

Apr. 19, 1999   (DE) .................................. 199 17 617

(51) Int. Cl.
   *A01N 43/653*   (2006.01)
   *C07D 249/12*   (2006.01)
(52) U.S. Cl. ..................................... 514/384; 548/263.2
(58) Field of Classification Search ................. 504/156; 514/384; 548/263.2
   See application file for complete search history.

(56) References Cited

U.S. PATENT DOCUMENTS

| | | | | |
|---|---|---|---|---|
| 4,927,839 A | * | 5/1990 | Parry et al. | 514/383 |
| 5,274,167 A | | 12/1993 | Lange et al. | |
| 5,468,751 A | * | 11/1995 | Kristiansen et al. | 514/256 |
| 5,650,519 A | * | 7/1997 | Lacroix et al. | 548/316.7 |
| 5,789,430 A | * | 8/1998 | Jautelat et al. | 514/384 |

FOREIGN PATENT DOCUMENTS

EP    0379917 A2    1/1990

* cited by examiner

*Primary Examiner* — Kamal Saeed
*Assistant Examiner* — Kristin Bianchi
(74) *Attorney, Agent, or Firm* — Baker Donelson Bearman, Caldwell & Berkowitz, PC

(57) ABSTRACT

A novel (−)-enantiomer of 2-[2-(1-chloro-cyclopropyl)-3-(2-chloro-phenyl)-2-hydroxypropyl]-2,4-dihydro-[1,2,4]-triazole-3-thione of the formula

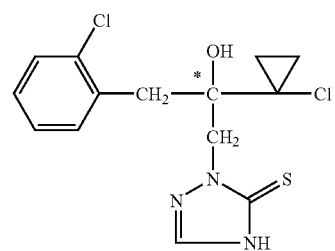

(I)

a process for preparing this novel active compound and its use as microbicide in crop protection and in the protection of materials.

19 Claims, No Drawings

# (−)-ENANTIOMER OF THE 2-[2-(1-CHLORO-CYCLOPROPYL)-3-(2-CHLOROPHENYL)-2-HYDROXYPROPYL]-2,4-DIHYDRO-[1,2,4]-TRIAZOLE-3-THIONE

RELATED APPLICATIONS

This application is a continuation of U.S. application Ser. No. 09/958,551, filed Oct. 10, 2001 now abandoned, which was filed under 35 U.S.C. 371 as a national stage application of International Application No. PCT/EP00/03066, filed Apr. 6, 2000, which was published in German as International Patent Publication WO 00/63188 on Oct. 26, 2000, which is entitled to the right of priority of German Patent Application No. 199 17 617.5, filed Apr. 19, 1999.

FIELD OF THE INVENTION

The present invention relates to the novel (−)-enantiomer of 2-[2-(1-chloro-cyclopropyl)-3-(2-chlorophenyl)-2-hydroxypropyl]-2,4-dihydro-[1,2,4]-triazole-3-thione, a process for its preparation and its use as microbicide.

BACKGROUND OF THE INVENTION

It is already known that the racemate of 2-[2-(1-chloro-cyclopropyl)-3-(2-chlorophenyl)-2-hydroxypropyl]-2,4-dihydro-[1,2,4]-triazole-3-thione has fungicidal properties (cf. WO 96-16 048). The activity of this substance is good; however, at very low application rates it is sometimes unsatisfactory.

This invention, accordingly, provides the novel (−)-enantiomer of 2-[2-(1-chloro-cyclopropyl)-3-(2-chlorophenyl)-2-hydroxypropyl]-2,4-dihydro-[1,2,4]-triazole-3-thione of the formula

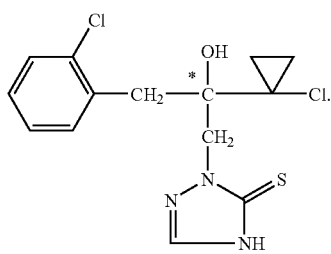

(I)

Here, the (−)-enantiomer is in each case to be understood as the enantiomer which rotates the plane of vibration of linear-polarized light of the sodium D-line to the left.

Furthermore, it has been found that the (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I) is obtained when a) racemic 2-[2-(1-chloro-cyclopropyl)-3-(2-chloro-phenyl)-2-hydroxypropyl]-2,4-dihydro-[1,2,4]-triazole-3-thione of the formula

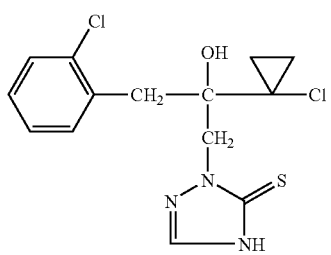

(Ia)

is chromatographed on a chiral stationary silica gel phase based on the optically active monomer N-methacryloyl-L-leucine-3-(2,4-dimethylpentyl)-amide using ethyl acetate as mobile phase at temperatures between 20° C. and 25° C., b) the eluate is concentrated under reduced pressure and c) the resulting product is recrystallized from toluene.

SUMMARY OF THE INVENTION

The (−)-enantiomer of 2-[2-(1-chloro-cyclopropyl)-3-(2-chlorophenyl)-2-hydroxy-propyl]-2,4-dihydro-[1,2,4]-triazole-3-thione has microbicidal activity.

DETAILED DESCRIPTION

Finally, it has been found that the novel (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I) has very good microbicidal properties and can be used both in crop protection and in the protection of materials for controlling undesirable microorganisms, such as fungi.

Surprisingly, the (−)-enantiomer of 2-[2-(1-chloro-cyclopropyl)-3-(2-chlorophenyl)-2-hydroxypropyl]-2,4-dihydro-[1,2,4]-triazole-3-thione of the formula (I) according to the invention has considerably better fungicidal activity than the corresponding (+)-enantiomer and the corresponding racemate, which is known as a highly effective active compound with fungicidal properties.

Some or all of the (−)-enantiomer according to the invention can be present in the "thiono" form of the formula

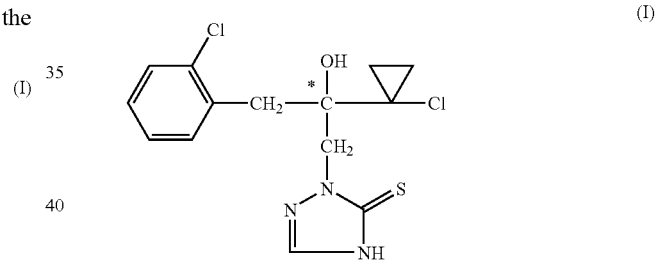

(I)

or in the tautomeric "mercapto" form of the formula

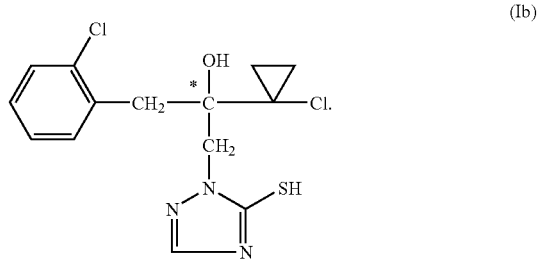

(Ib)

For the sake of simplicity, only the "thiono" form is shown in each case.

In the formula (I) and (Ib), the asymmetrically substituted carbon atom is in each case marked by an (*).

The racemic 2-[2-(1-chloro-cyclopropyl)-3-(2-chloro-phenyl)-2-hydroxypropyl]-2,4-dihydro-[1,2,4]-triazole-3-thione of the formula (Ia) which is required as starting material for carrying out the process according to the invention is known (cf. WO 96-16 048).

When carrying out the process according to the invention, methods of preparative chromatography, preferably the method of high-performance liquid chromatography (=HPLC), are employed. The separating material used for this purpose is known (cf. EP-A 0 397 917).

The substance content in the eluate is determined by photometric detection. The collected eluate fractions are analyzed for enantiomeric purity. All the fractions which contain the same enantiomer are pooled and concentrated under reduced pressure. The resulting product is then recrystallized from toluene.

The product that elutes first is the (−)-enantiomer according to the invention. From other fractions which elute later, the corresponding (+)-enantiomer can be isolated.

The active compound according to the invention has potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae; and
Pseudocercosporella species, such as, for example, Pseudocercosporella herpotrichoides.

The fact that the active compound is well tolerated by plants at the concentrations required for controlling plant diseases permits the treatment of aerial parts of plants, of propagation stock and seeds, and of the soil The active compound according to the invention can be employed particularly successfully for controlling diseases in fruit and vegetable growing and viticulture, such as, for example, against powdery mildew fungi, such as Sphaerotheca, Uncinula, against Erysiphe species and leaf spot, such as Venturia and Alternaria species. Cereal diseases such as Erysiphe, Leptosphaeria or Pyrenophora species, and rice diseases, such as Pyricularia species, are also controlled very successfully.

The active compound according to the invention is also suitable for increasing the yield of crops. Moreover, it has reduced toxicity and is tolerated well by crops.

In the protection of materials, the active compound according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
Alternaria, such as Alternaria tenuis,
Aspergillus, such as Aspergillus niger,
Chaetomium, such as Chaetomium globosum,
Coniophora, such as Coniophora puetana,
Lentinus, such as Lentinus tigrinus,
Penicillium, such as Penicillium glaucum,
Polyporus, such as Polyporus versicolor,
Aureobasidium, such as Aureobasidium pullulans,
Sclerophoma, such as Sclerophoma pityophila,
Trichoderma, such as Trichoderma viride,
Escherichia, such as Escherichia coli,
Pseudomonas, such as Pseudomonas aeruginosa, and
Staphylococcus, such as Staphylococcus aureus.

The active compound can be converted to the customary formulations, such as solutions, emulsions, suspensions, powders, foams, pastes, granules, aerosols and microencapsulations in polymeric substances and in coating compositions for seed, and ULV cool and warm fogging formulations.

These formulations are produced in a known manner, for example by mixing the active compound with extenders, that is liquid solvents, liquefied gases under pressure, and/or solid carriers, optionally with the use of surfactants, that is emulsifiers and/or dispersants and/or foam formers. If the extender used is water, it is also possible to use for example organic solvents as auxiliary solvents. The suitable liquid solvents are, essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins, and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compound according to the invention can be used as such or in its formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components Examples of co-components in mixtures are the following compounds:

Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB), quinoxyfen,
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801, ∀-(1,1-dimethylethyl)-∃-(2-phenoxyethyl)-1H-1,2,4-triazole-1-ethanol,
∀-(2,4-dichlorophenyl)-∃-fluoro-∃-propyl-1H-1,2,4-triazole-1-ethanol,
∀-(2,4-dichlorophenyl)-∃-methoxy-∀-methyl-1H-1,2,4-triazole-1-ethanol,
∀-(5-methyl-1,3-dioxan-5-yl)-∃-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-∀-(methoxyimino)-N-methyl-2-phenoxy-phenylacetamide,
isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-∃-D-glycopyranosyl)-∀-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propinyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxymethanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopemmethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispemmethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimphos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazophos, isofenphos, isoxathion, ivermectin, lambda-cyhalothrin, lufenuron, malathion, mecarbam, metaldehyde, methamidophos, *Metharhizium anisopliae, Metharhizium flavoviride*, metlhidathion, methiocarb, metlhomyl, methoxyfenozide, metolcarb, metoxadiazone, mevinphos, milbemectin, monocrotophos, naled, nitenpyram, nithiazine, novaluron, nuclear polyhedrosis viruses, omethoat, oxamyl, oxydemethon M,

*Paecilomyces fumosoroseus*, parathion A, parathion M, pennethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypemmethrin, zolaprofos, (1R-cis)-[5-(phenylmethyl)-3-furanyl]-methyl-3-[(dihydro-2-oxo-3(2H)-furanylidene)-methyl]2,2-dimethylcyclopropanecarboxylate, (3-phenoxyphenyl)-methyl 2,2,3,3-tetramethylcyclopropanecarboxylate, 1-[(2-chloro-5-thiazolyl)methlyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate, It is also possible to admix other known active compounds, such as herbicides, fertilizers and growth-regulating substances.

The active compound can be used as such or in the form of its formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compound by the ultra-low-volume method or to inject the active compound formulation, or the active compound itself, into the soil. The seed of the plants can also be treated.

When using the active compound according to the invention as fungicide, the application rate can be varied within a relatively wide range, depending on the type of application. In the treatment of parts of plants, the application rates of active compound are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

The compositions used for the protection of industrial materials generally comprise an amount of 1 to 95%, preferably 10 to 75%, of the active compounds.

The use concentrations of the active compound according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The activity and the spectrum of activity of the active compound to be used according to the invention in the protection of materials, or of the compositions, concentrates or quite generally formulations prepared therefrom, can be increased by adding, if appropriate, other antimicrobially active compounds, fungicides, bactericides, herbicides, insecticides or other active compounds to widen the spectrum of activity or to obtain particular effects, such as, for example, additional protection against insects. These mixtures may have a wider spectrum of activity than the compounds according to the invention.

The preparation and the use of the active compound according to the invention are shown in the examples below.

PREPARATION EXAMPLE (I)

300 g of racemic 2-[2-(1-chloro-cyclopropyl)-3-(2-chlorophenyl)-2-hydroxypropyl]-2,4-dihydro-[1,2,4]-triazole-3-thione are separated in portions of 0.2 g on a chiral stationary silica gel phase (CSP) based on the optically active monomer N-methacryloyl-L-leucine-3-(2,4-dimethyl-pentyl)-amide using ethyl acetate as mobile phase at room temperature (about 23° C.), by the HPLC method. The eluate is subjected to photometric detection. Specifically, the preparation separation is carried out under the conditions outlined below.

| Column: | CSP as above, 10 μm; 570 * 50 mm ID |
|---|---|
| Mobile phase: | ethyl acetate |
| Flow rate: | 100 ml/min |
| Detection: | UV; 254 nm |
| Sample application: | 0.2 g dissolved in 20 ml of ethyl acetate |

The fractions which contain the same enantiomer are pooled and concentrated under reduced pressure. The resulting product is then recrystallized from toluene.

Under the stated conditions, the laevorotatory enantiomer elutes first, followed by the dextrorotatory enantiomer.

This gives 117 g of the (−)-enantiomer of 2-[2-(1-chlorocyclopropyl)-3-(2-chlorophenyl)-2-hydroxypropyl]-2,4-dihydro-[1,2,4]-triazole-3-thione in the form of a solid of melting point 123 to 124° C.

Specific Rotation:

$[\alpha]_D^{20} = -55.5°$ (10 mg/1 ml of chloroform)

Analogously, 119 g of the (+)-enantiomer are obtained in the form of a solid of melting point 122-123° C.

Specific Rotation:

$[\alpha]_D^{20} = 54.9°$ (10 mg/1 ml of chloroform)

USE EXAMPLES

Example A

Cochliobolus Sativus Test (Barley)/Protective

| Solvent: | 10 parts by weight of N-methyl-pyrrolidone |
|---|---|
| Emulsifier: | 0.6 parts by weight of alkylaryl polyglycol ether |

To produce a suitable preparation of active compound, 1 part by weight of compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of Cochiliobolus sativus. The plants remain in an incubation cabin at 20° C. and 100% relative atmospheric humidity for 48 hours.

The plants are placed in a greenhouse at a temperature of 20° C. and a relative atmospheric humidity of approximately 80%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE A

Cochliobolus sativus test (barley)/protective

| Active compound | Active compound application rate in g/ha | Efficacy in % |
|---|---|---|
| Known from WO 96-16 048 | 250 | 66 |
|  | 125 | 59 |
| According to the invention: | 250 | 75 |
| (I) laevorotatory | 125 | 75 |

Example B

Podosphaera Test (Apple)/Protective

| Solvent: | 47 parts by weight of acetone |
|---|---|
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple powdery mildew pathogen *Podosphaera leucotricha*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE B

| Podosphaera test (apple)/protective | | |
|---|---|---|
| Active compound | Active compound application rate in g/ha | Efficacy in % |
| Known from WO 96-16 048 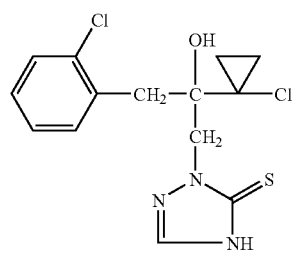 | 10 | 60 |
| According to the invention 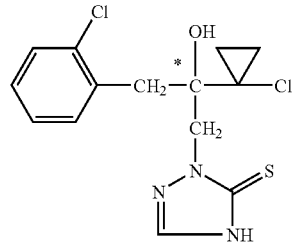 (I) laevorotatory | 10 | 78 |

Example C

*Uncinula* Test (Vine)/Protective

| | |
|---|---|
| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the *Uncinula necator*. The plants are then placed in a greenhouse at approximately 23° C. and a relative atmospheric humidity of approximately 70%.

Evaluation is carried out 14 days after the inoculation. 0% means an efficacy which corresponds to that of the control, whereas an efficacy of 100% means that no infection is observed.

Active compounds, application rates and test results are shown in the table below.

TABLE C

| Uncinula test (vine)/protective | | |
|---|---|---|
| Active compound | Active compound application rate in g/ha | Efficacy in % |
| Known from WO 96-16 048 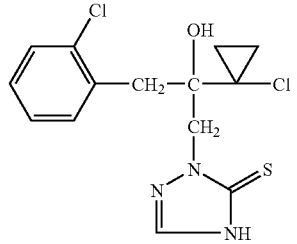 | 10 | 47 |
| According to the invention 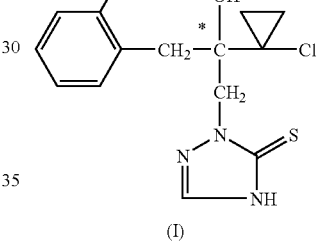 (I) levorotatory | 10 | 84 |

Example D

*Venturia* Test (Apple)/Curative

| | |
|---|---|
| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab pathogen *Venturia inaequalis*. The plants remain in an incubation cabin at approximately 20° C. and 100% relative atmospheric humidity for 1 day and are then placed in a greenhouse. After a defined number of hours, the plants are sprayed with the preparation of active compound at the stated application rate.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

Active compounds, application rates and test results are shown in the table below.

TABLE D

Venturia test (apple)/curative

| Active compound | Active compound application rate in g/ha | Efficacy in % |
|---|---|---|
| Known from WO 96-16 048 | 1 | 79 |
| According to the invention: | 1 | 91 |

(I) laevorotatory

Example E

*Pyricularia* Test (Rice)/Protective

| Solvent: | 2.5 parts by weight of acetone |
| Emulsifier: | 0.06 parts by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound at the stated application rate. After the spray coating has dried on, the plants are inoculated with an aqueous spore suspension of *Pyricularia oryzae*. The plants are then placed in a greenhouse at a relative atmospheric humidity of 100% and 25° C.

Evaluation is carried out 4 days after the inoculation. 0% means an efficacy which corresponds to that of the control, whereas an efficacy of 100% means that no infection is observed.

Active compounds, application rates and test results are shown in the table below.

TABLE E

*Pyricularia* test (rice)/protective

| Active compound | Active compound application rate in g/ha | Efficacy in % |
|---|---|---|
| Known from WO 96-16 048 | 375 | 30 |
| According to the invention: | 375 | 90 |

(I) laevorotatory

The invention claimed is:

1. A method for controlling the growth of at least one microorganism comprising applying to the microorganism and/or its habitat a composition having an effective amount of (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I)

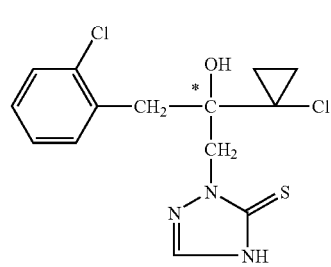

wherein the composition is substantially free of (+)-enantiomer of 2-[2-(1-chloro-cyclopropyl)-3-(2-chloro-phenyl)-2-hydroxypropyl]-2,4-dihydro-[1,2,4]-triazole-3-thione.

2. The method of claim 1, wherein the microorganism is selected from the group consisting of fungi, bacteria, yeasts, algae, slime organisms, and combinations thereof.

3. A method according to claim 1 for controlling fungi that infect plants comprising applying 0.1 to 10,000 g per hectare of the (−)-enantiomer of 2-[2-(1-chloro-cyclopropyl)-3-(2- chloro-phenyl)-2-hydroxypropyl]-2,4-dihydro-[1,2,4]-triazole-3-thione to the aerial parts of plants or to the soil in which the plants are grown.

4. A method according to claim 1 for controlling fungi that infect plants comprising applying the (−)-enantiomer of 2-[2-(1-chloro-cyclopropyl)-3-(2-chloro-phenyl)-2-hydroxypropyl]-2,4-dihydro-[1,2,4]-triazole-3-thione to seed of the plant at a rate of 0.001 to 50 g per kilogram of the seed.

5. A method according to claim 1 for protecting an industrial material against the growth of microorganisms comprising applying 0.001 to 5% by weight, based on the industrial material, of the (−)-enantiomer of 2-[2-(1-chloro-cyclopropyl)-3-(2-chloro-phenyl)-2-hydroxypropyl]-2,4-dihydro-[1,2,4]-triazole-3-thione to the industrial material.

6. A method according to claim 5 wherein the industrial material is an adhesive, size, paper, board, textile, leather, wood, paint, plastic article, cooling lubricant, or heat-transfer liquid.

7. A method for controlling microorganisms in crop protection and protection of materials comprising administering a composition comprising (−)-enantiomer of 2[2 (1-chloro-cyclopropyl)-3-(2-chloro-phenyl)-2-hydroxypropyl]-2,4-dihydro-[1,2,4]-triazole-3-thione of the formula (I)

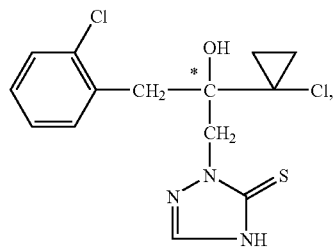

wherein the composition is substantially free of (+)-enantiomer of 2-[2-(1-chloro-cyclopropyl)-3-(2-chloro-phenyl)-2-hydroxypropyl]-2,4-dihydro-[1,2,4]-triazole-3-thione, and wherein the composition is administered at an application rate of the (−)-enantiomer of:

from about 0.1 to about 10,000 g/ha for plants;
from about 0.001 to about 50 g/kg for seed;
from about 0.1 to about 10,000 g/ha for soil; or
from a concentration of about 0.001% to about 5% by weight, for the material.

8. The method of claim 3, wherein the composition is administered at an application rate of:

from about 10 to about 1,000 g/ha for plants;
from about 0.01 to about 10 g/kg for seed;
from about 1 to about 5,000 g/ha for soil; or
from a concentration of about 0.05% to about 1.0% by weight, for the material.

9. A method for controlling the growth of at least one microorganism comprising applying to the microorganism and/or its habitat a composition having an effective amount of (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I)

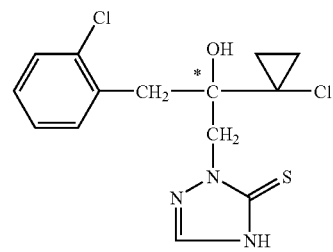

wherein application of the composition is carried out in the substantial absence of (+)-enantiomer of 2-[2-(1-chloro-cyclopropyl)-3-(2-chloro-phenyl)-2-hydroxypropyl]-2,4-dihydro-[1,2,4]-triazole-3-thione.

10. The method of claim 9, wherein the microorganism is selected from the group consisting of fungi, bacteria, yeasts, algae, slime organisms, and combinations thereof.

11. A method according to claim 9 for controlling fungi that infect plants comprising applying 0.1 to 10,000 g per hectare of the (−)-enantiomer of 2-[2-(1-chloro-cyclopropyl)-3-(2-chloro-phenyl)-2-hydroxypropyl]-2,4-dihydro-[1,2,4]-triazole-3-thione to the aerial parts of plants or to the soil in which the plants are grown.

12. A method according to claim 9 for controlling fungi that infect plants comprising applying the (−)-enantiomer of 2-[2-(1-chloro-cyclopropyl)-3-(2-chloro-phenyl)-2-hydroxypropyl]-2,4-dihydro-[1,2,4]-triazole-3-thione to seed of the plant at a rate of 0.001 to 50 g per kilogram of the seed.

13. A method according to claim 9 for protecting an industrial material against the growth of microorganisms comprising applying 0.001 to 5% by weight, based on the industrial material, of the (−)-enantiomer of 2-[2-(1-chloro-cyclopropyl)-3-(2-chloro-phenyl)-2-hydroxypropyl]-2,4-dihydro-[1,2,4]-triazole-3-thione to the industrial material.

14. A method according to claim 13 wherein the industrial material is an adhesive, size, paper, board, textile, leather, wood, paint, plastic article, cooling lubricant, or heat-transfer liquid.

15. A method for controlling microorganisms in crop protection and protection of materials comprising administering a composition comprising (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I)

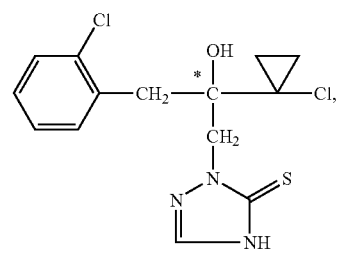

wherein application of the composition is carried out in the substantial absence of (+)-enantiomer of 2-[2-(1-chloro-cyclopropyl)-3-(2-chloro-phenyl)-2-hydroxypropyl]-2,4-dihydro-[1,2,4]-triazole-3-thione, and wherein the composition is administered at an application rate of the (−)-enantiomer of:

from about 0.1 to about 10,000 g/ha for plants;
from about 0.001 to about 50 g/kg for seed;
from about 0.1 to about 10,000 g/ha for soil; or from a concentration of about 0.001% to about 5% by weight, for the material.

16. The method of claim 15, wherein the composition is administered at an application rate of:
from about 10 to about 1,000 g/ha for plants;
from about 0.01 to about 10 g/kg for seed;
from about 1 to about 5,000 g/ha for soil; or
from a concentration of about 0.05% to about 1.0% by weight, for the material.

17. The (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I)

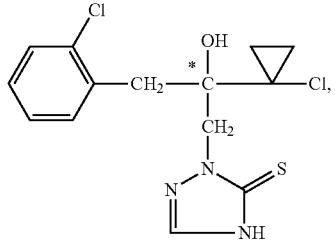

(I)

substantially free of the (+)-enantiomer of 2-[2-(1-chloro-cyclopropyl)-3-(2-chloro-phenyl)-2-hydroxypropyl]-2,4-dihydro-[1,2,4]-triazole-3-thione.

18. The (−)-enantiomer of claim 17, wherein said (−)-enantiomer is produced by HPLC chromatography of racemic 2-[2-(1-chloro-cyclopropyl)-3-(2-chloro-phenyl)-2-hydroxypropyl]-2,4-dihydro-[1,2,4]-triazole-3-thione on a chiral stationary silica gel phase based on the optically active monomer N-methacryloyl-L-leucine-3-(2,4-dimethyl-pentyl)-amide using ethyl acetate as mobile phase at temperatures between 20° C. and 25° C.

19. A method for obtaining the (−)-enantiomer of 2-[2-(1-chloro-cyclopropyl)-3-(2-chloro-phenyl)-2-hydroxypropyl]-2,4-dihydro-[1,2,4]-triazole-3-thione of the formula (I)

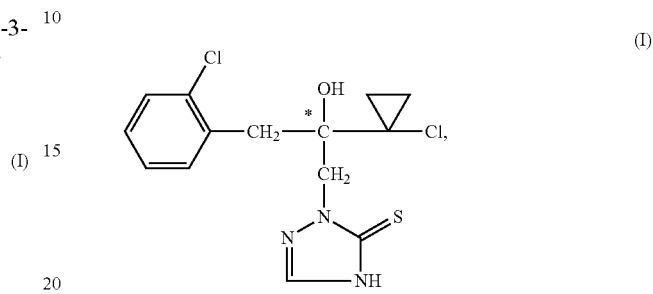

substantially free of the (+)-enantiomer of 2-[2-(1-chloro-cyclopropyl)-3-(2-chloro-phenyl)-2-hydroxypropyl]-2,4-dihydro-[1,2,4]-triazole-3-thione, comprising performing HPLC chromatography of racemic 2-[2-(1-chloro-cyclopropyl)-3-(2-chloro-phenyl)-2-hydroxypropyl]-2,4-dihydro-[1,2,4]-triazole-3-thione on a chiral stationary silica gel phase based on the optically active monomer N-methacryloyl-L-leucine-3-(2,4-dimethyl-pentyl)-amide using ethyl acetate as mobile phase at temperatures between 20° C. and 25° C.

* * * * *